United States Patent [19]

Broder et al.

[11] Patent Number: 4,935,427
[45] Date of Patent: Jun. 19, 1990

[54] PYRIMIDINE AND PURINE 1,2-BUTADIENE-4-OLS AS ANTI-RETROVIRAL AGENTS

[75] Inventors: Samuel Broder; Seiji Hayashi, both of Bethesda; Hiroaki Mitsuya, Rockville, all of Md.; Jiri Zemlicka, Warren; Shashikant Phadtare, Detroit, both of Mich.

[73] Assignee: The United States of America as represented by the Department of Health and Human Services, Washington, D.C.

[21] Appl. No.: 140,269

[22] Filed: Dec. 31, 1987

[51] Int. Cl.$^5$ .................. A61K 31/52; A61K 31/505; C07D 473/34; C07D 239/47
[52] U.S. Cl. ..................... 514/261; 514/274; 544/265; 544/276; 544/277; 544/317
[58] Field of Search .............. 544/277, 276, 265, 182, 544/280, 317, 254; 514/261, 258, 262, 274, 242

[56] References Cited

U.S. PATENT DOCUMENTS 3,664,991  5/1972  Kaye ........................ 544/277 X
4,393,064  7/1983  DeGraw, Jr. et al. ............ 514/249
4,798,833  1/1989  Johansson et al. .............. 514/262

FOREIGN PATENT DOCUMENTS 55239  6/1982  European Pat. Off. .
146516  6/1985  European Pat. Off. .

OTHER PUBLICATIONS

Zemlicka, Nucleosides & Nucleotides, 3(3), 245–264 (1984).
Mitsya, et al., Proc. Natl., Acad. Sci. U.S.A., vol. 82, pp. 7096–7100 (10/85).
Phadtare, et al., "Nucleic Acids Symp. Ser." 1987, 18(Symp. Chem. Nucleic Acid Compon., 7th, 1987), pp. 25–28.
Hayashi, et al., Proc. Natl. Acad. Sci. U.S.A., 85(16), pp. 6127–6131 08/88.

Primary Examiner—Diana G. Rivers
Attorney, Agent, or Firm—Glenna Hendricks; Robert Benson

[57] ABSTRACT

Compounds which are active against retroviruses have the following formula

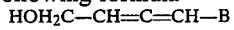

HOH$_2$C—CH=C=CH—B wherein B is a purine or pyrimidine heterocyclic ring which is preferably selected from the group consisting of cytosine, 5-halo substituted cytosine, 5-alkyl substituted cytosine, 6-aminopurine, 2,6-diaminopurine, 6-hydroxypurine, 2-amino-6-hydroxypurine, 3-deazapurines, 7-deazapurines, 8-azapurines, and 6-azapyrimidines.

4 Claims, 3 Drawing Sheets

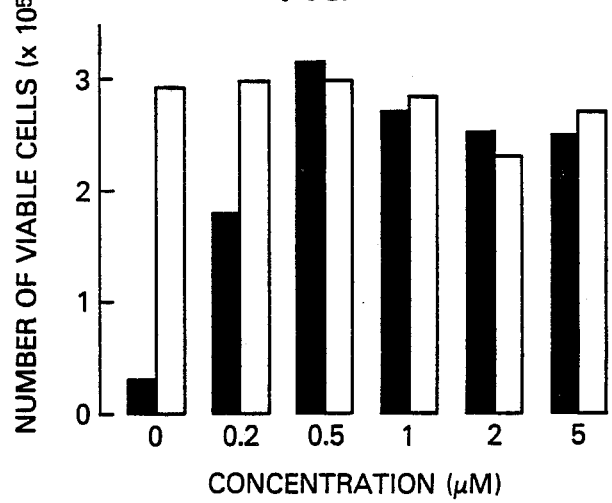
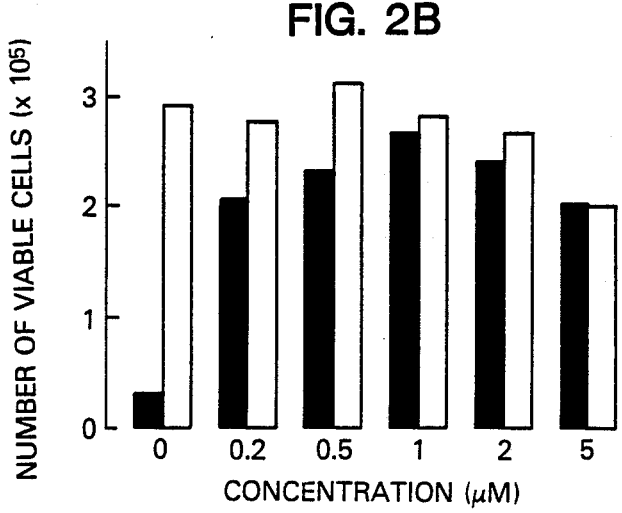

PYRIMIDINE AND PURINE 1,2-BUTADIENE-4-OLS AS ANTI-RETROVIRAL AGENTS

FIELD OF THE INVENTION

The present invention relates to original pyrimidine and purine compounds which have activity against retroviruses.

BACKGROUND OF THE INVENTION

Human immunosuppressive virus (HIV), which is also called human T-lymphotropic virus type III (HTLV-III), lymphadenopathy-associated virus (LAV), or AIDS-associated retrovirus (ARV) is cytopathic for helper/inducer T-cells and is the etiologic agent of acquired immunodeficiency syndrome (AIDS) and related diseases.

Various alkyl derivatives of pyrimidines and purines and analogues thereof have been found to exhibit a wide range of biological activity, cf. Keller et al., *Biochem. Pharmacol.* 30, 3071 (1981); European Patent No. 55,239; European Patent No. 146,516; Hua et al., *J. Med. Chem.* 30, 198 (1987); Phadtare et al., *J. Med. Chem.* 30, 437 (1987). Additionally, 2',3'-dideoxynucleosides and related compounds have been found effective against HIV, cf. Mitsuya et al., *Proc. Nat. Acad. Sci. USA* 83, 1911 (1986); Mitsuya et al. *Proc. Nat. Acad. Sci. USA*, 82, 7096 (1985); Herdewijn et al., *J. Med. Chem.* 30, 1270 (1987); Mitsuya et al. *Nature* 325, 773 (1987); Mitsuya et al. in "AIDS, Modern Concepts and Therapeutic Challenges" (S. Broder, Ed.), 1987, Marcel Dekker, New York, p.303.

SUMMARY OF THE INVENTION

It is an object of the present invention to overcome the above-noted deficiencies in the prior art.

It is another object of the present invention to provide compounds having a novel structure.

It is a further object of the present invention to provide compounds which have novel activity against HIV, the etiologic agent of AIDS, as well as against mammalian retroviruses.

It is yet another object of the present invention to provide a synthesis method for the compounds of the present invention.

It is a still further object of the present invention to provide pharmaceutical compositions for use in AIDS therapy.

The present invention relates to 1,2-butadiene-4-ols which are substituted in the 1-position by various heterocyclic groups and pharmacologically acceptable acid salts thereof. These compounds have been found to be useful antiretroviral agents. The compounds of the invention are effective against human immunosuppressive virus (HIV) as well as against other mammalian retroviruses.

The compounds of the present invention have the following formula:

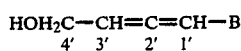   Formula 1 wherein B is a heterocyclic ring derived from a pyrimidine or purine moiety such as cytosine, 5-chloro, 5-bromo-, 5-iodo-, and 5-fluorocytosine, 5-methyl, cytosine, and related 5-alkyl derivatives containing a saturated or unsaturated alkyl group such as 5-ethyl, 5-ethenyl, and 5-ethynyl functions, 6-aminopurine (adenine), 2,6-diaminopurine, 6-hydroxypurine (hypoxanthine) and 2-amino-6-hydroxypurine (guanine). Heterocyclic substituents on B also include 3- and 7-deazapurines, such as 3-deazaadenine and 7-deazaadenine, and 8-azapurines, such as 8-azaadenine, as well as 6-azapyrimidines, such as 6-azacytosine.

Compositions useful for treating retroviral infections, such as HIV causing an acquired immunodeficiency syndrome, contain an effective amount of at least one compound of formula 1 or a pharmaceutically acceptable salt thereof.

The present invention also includes a method for synthesizing compounds of formula 1 wherein B is a heterocyclic ring derived from a pyrimidine or a purine moiety such as cytosine, 5-halocytosine (wherein halo is bromo, chloro, iodo, or fluoro), 5-methylcytosine and related alkyl derivatives containing a saturated or unsaturated alkyl group at the 5-position, wherein the alkyl is selected from the group consisting of ethyl, ethenyl, and ethynyl; 6-aminopurine (adenine); 2,6-diamnopurine, 6-hydroxypurine (hypoxanthine), 2-amino,6-hydroxypurine (guanine), 3-and 7-deazapurines, such as 3- and 7-deazaadenine; 8-azapurines such as 8-azaadenine; and 6-azapyrimidines, such as 6-azacytosine.

BRIEF DESCRIPTION OF THE DRAWINGS

FIG. 2 shows the inhibition of the cytopathic effect of HIV against ATH8 cells by cytallene.

DETAILED DESCRIPTION OF THE INVENTION

Figure 1A:
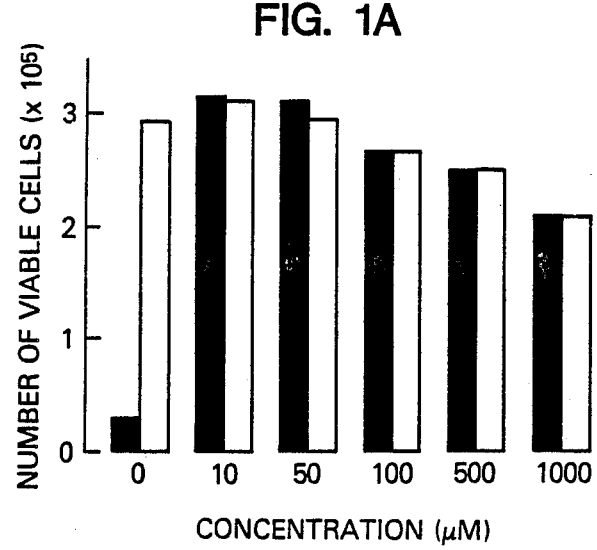
FIG. 1 shows the inhibition of the cytopathic effect of HIV against ATH8 cells by adenallene.

The compounds of the present invention which have been found to be effective against mammalian retroviruses are compounds of formula 1 wherein B represents a heterocyclic ring derived from a pyrimidine or purine moiety. Among the groups that may comprise the heterocyclic ring are the following: cytosine, 5-halocytosine, wherein halo is selected form the group consisting of bronmor, chloro, iodo, and fluoro; 5-alkylcytosinse wherein the alkyl is selected from the group consisting of ethyl, methyl, ethenyl, and ethynyl; substituted purines selected from the group consisting of 6-aminopurine, 2,6-diaminopurine, 6-hydroxypurine, and 2-amino,6-hydroxy purine; 3- and 7-deazapurine; and 6-azapyrimidines.

The preferred compounds of the present invention are $N^1$-( 4-hydroxy-1,2-butadien-1-yl)cytosine (cytallene) wherein in formula 1, B = cytosine-$N^1$-yl 7 and $N^9$-(4-hydroxy-1,2-butadiene-1-yl) adenine (adenallane), wherein B = adenin-$N^9$-yl.

The nomenclature of the compounds of the present invention follows standard conventions The numbering of the 1,2-butadien-4-ol portion attached to the heterocyclic ring B is shown in Formula 1. The pyrimidine and purine rings are numbered as indicated below:

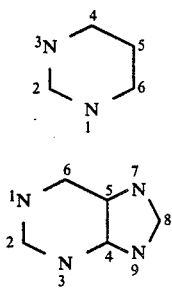

It is understood that heterocyclic rings containing hydroxy and amino groups are tautomeric with the corresponding oxo and imino compounds.

It should be noted that there in an inherent asymmetry of the 1,3-disubstituted allene (1,2-propadiene) system as shown in Formula 1. Structure 1 may be viewed as 1-substituted-3-hydroxymethylallene. Compounds of the present invention are therefore racemic mixtures of two optical antipodes which may be resolved by conventional resolution methods, such as chromatography or fractional crystallization of suitable diastereoisomeric derivatives such as salts or esters with optically active acids (camphor-10-sulfonic acid, methoxyacetic acid, dibenzoyltartaric acid, 6-methoxy-2-naphthyl-2-propanoic acid, etc.). The resultant diastereoisomeric salts or esters may then be transformed to optically active compounds of Formula 1.

The synthesis of the compounds of the present invention is summarized in Scheme 1, below A heterocyclic base B-H (purine or pyrimidine) is alkylated with 1,4-dichloro-2-butyne (2, usually an excess thereof) in the presence of suitable basic agent such as $K_2CO_3$ and a solvent, e.g., dimethylsulfoxide. The resultant 4-chloro-2-butynyl pyrimidine or purine, 3, is then hydrolyzed in acid, such as 0.1M HCl to the corresponding 4-hydroxy derivative 4. The latter is then isomerized in the presence of a base such as NaOH or potassium tert-butoxide, to the corresponding allene derivative, 1.

Scheme 1

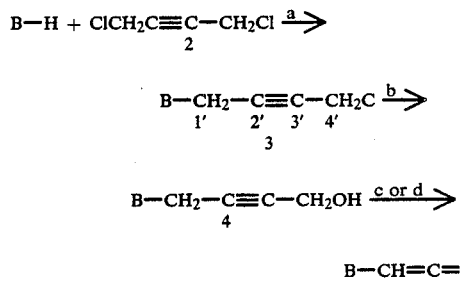

Hypozanthine derivative 1, where B=hypoxanthine-$N^9$-yl, is obtained by deamination of the adenine precursor 1 wherein B=adenin-$N^9$-yl with adenosine deaminase, as shown in Scheme 2.

Scheme 2

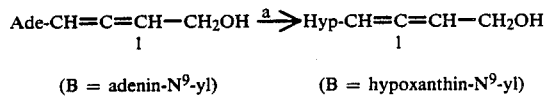

(B = adenin-$N^9$-yl)  (B = hypoxanthin-$N^9$-yl)

EXAMPLES

Example 1, Synthesis of Adenallene 1
(B=ademin-N-yl)

A mixture of 1.35 g, 10 mmol adenine, 2.76 g, 20 mmol potassium carbonate, and 4.88 g, 40 mmol of 1,4-dichloro-2-butyne was magnetically stirred in 50 ml of dimethylsulfoxide for 18 hours at room temperature. The solvent was evaporated in vacuo (oil pump), the residue was washed with 30 ml, 9:1 dichloromethane-methanol (S1), the solids were filtered off, and the filtrate was evaporated. The crude material was flash-chromatographed on a short column of silic gel in solvent S1. The fractions containing the product were combined and were evaporated to give 1.17 grams, or 53%, of compound 3, wherein B=adenin-$N^9$-yl.

An analytical sample was obtained upon crystallization from ethyl acetate-methanol (95:5). The sample was homogeneous on thin layer chromatography (S1), mp. 199°–201° C. UV (ethanol) max 260 nm ( 15,600). $^1$H-NMR (300 MHz, CD$_3$SOCD$_3$), 8.18 and 8.15 (2s, 2, H-2, and H-8, purine), 7.29 (s, 2, NH$_2$), b 5.11 (t, 2, H-1'), 4,47 (t,2,H-4').

Electron mass-impact spectrum was as follows: 221 (13.2, M), 186 (100.0, M-Cl), 159 (19.2).

Adenine peaks: 135, 108, 80, and 66.

Anal.—Calculated for C$_9$H$_8$ClN$_5$: C, 48.76; H, 3.63; Cl, 15.99; N, 31.59. Found, C, 48.82; H, 3.82; Cl, 16.10.

$N^9$-(4-hydroxy-2-butyn-1-yl)adenine (compound 4, where B=adenine $N^9$-yl).

Five mmol, or 1.1 g, of compound 3, wherein B=adenin-$N^9$-yl, was refluxed in 50 ml of 0.1M HCl for eighteen hours. The solution was cooled and neutralized with sodium hydroxide, whereupon the solvent was evaporated. The residue was chromatographed on a silica gel column in solvent S1. The major fraction afforded after evaporation was product 4, wherein B=adenin-$N^9$-yl. The product yield was 68%, or 0.68 g. An analytical sample was obtained after crystallization from 9:1 methanol-water, mp. 221°–223° C.

UV (0.05M Na$_2$HPO$_4$, pH 7) max 260 nm (13,900), 208 (20,200).

$^1$H-NMR (CD$_3$SOCD$_3$) , 8.16 (2s 2, H-2 and H-8 purine), 7.21 (s, 2, NH$_2$), 5.16 (t, 1, OH), 5.03 (t,2, H-1'), 4.07 (m, 2, H-4').

Electron-impact mass spectrum: 204 (11.5, M+H), 203 (30.8, M), 202 (100.0 M−H), 186 (41.6, M−OH), 174 (26.4, M−CH$_2$OH), 158 (14.0), 147 (10.3).

Adenine peaks: 135, 119, 108, 81, 66, and 53.

Calculated for C$_9$H$_9$N$_5$R: C, 53.19; H, 4.46; N, 34.46. Found: C, 53.17; H, 4.40; N, 34.51.

$N^9$-(4-Hydroxy-1,2-butadien-1-yl)adenine.

Two methods were used to synthesize this compound In Method A, compound 4, where B=adenin-$N^9$-yl was refluxed in 25 ml of 0.1M NaOH for thirty minutes. The progress of the isomerization was followed by thin layer chromatography in solvent S1. After thirty minutes, an equilibrium was reached with about 50% of the product present The solution was then cooled to 0°–5° C. in an ice bath, and the pH was adjusted with 0.1M HCl to 7, using a pH meter. The mixture was evaporated in vacuo and the resultant solid was chromatographed on a silica gel column in solvent S1.

The product-containing fractions were pooled and were evaporated to give compound 0.2 grams of compound 1, a 33% yield Crystallization from 9:1 ethyl acetate-methanol afforded an analytical sample having a melting point of 198°–190° C.

UV (pH 7) max 260 nm ( 12,100), 207 ( 22,400).

$^1$H-NMR (CD$_3$SOCD$_3$) , 8.17 (2s, 2, H2 and H8 purine), 7.37 (m, 3, NH2+H-1'), 6.22 (q, 1, H-3'), 5.17 (t, 1 OH), 4.12 (m, 2, H-4').

$^{13}$C-NMR 195.63 (C-2'), 156.0 (C-1'), 152.9 (C-3'), 148.3 (C-4').

Adenine peaks: 138.3, 118.8, 105.7, 93.7, and 58.8.

Electron-impact mass spectrum: 203 (73.4, M), 186 (100.0, M, OH), 176 (81.2, M*—CH$_2$=CH, for M* see Scheme 3) 159 (28.0), 147 (17.7).

Adenine peaks: 135, 120, 108, 81, 66, and 54.

Calculated for C$_9$H$_9$N$_5$O: C, 53.19; H, 4.46; N, 34.46. Found: C, 53.41; H, 4.44; N, 34.66.

chromatographed on a silica gel column in 4:1 dichloromethane-methanol, solvent S2, to give a 60% yield, 538 mg, of compound 4.

Crystallization from 3:2 ethyl acetate-methanol yielded an analytical sample, melting point 191°–193° C.

UV (pH 7) max 271 nm (9,500), 204 (14,600). $^1$H-NMR (CD$_3$SOCD$_3$) , 7.63 (d, 1, H$_6$- cytosine), 7.17 (s, 2, HN$_2$), 5.70 (d, 1, H$_5$- cytosine), 5.22 (t, 1, OH), 4.49 (t, 2, 1'—CH$_2$), 4.06 (m, 2, 4'-CH$_2$).

Electron-impact mass spectrum 180 (12.4, M+H), 179 (19.1, M), 162 (100.0, M−OH), 149 (48.0, M−CH$_2$OH), 133 (24.2).

Cytosine peaks: 111, 92, 80, 67 and 52.

Calculated for C$_8$H$_9$N$_3$O$_2$: C, 53.62; H, 5.06; N, 23.45. Found: C, 53.81; H, 5.15; N, 23.39.

Scheme 3
Rearrangement of molecular ion derived from adenallene 1 (B = adenin-N$^9$-yl)

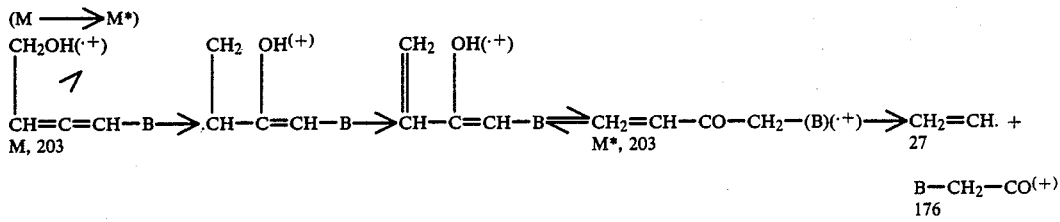

In method B, a solution of 203 mg, or 1 mmol, of compound 4, where B is adenin-N$^9$-yl in 15 ml of dimethylformamide was cooled to −10° C. Freshly sublimed potassium tert-butoxide was then added in the amount of 224 mg, or 2 mmol, and the mixture was stirred under nitrogen for 1.5 hour. The reaction was quenched by adding 10 ml of water to the mixture.

The solvents were evaporated in vacuo with an oil pump, and the resultant material was chromatographed on a silica gel column in solvent S1. The fractions containing the product were pooled and evaporated to give 100 mg (50% yield) of compound 1, which was identical by thin layer chromatography, melting point, and ultraviolet spectrum with a sample obtained by method A.

Example 2, Synthesis of Cytallene, where B is cytosin-N$^1$-yl

N$^1$-(4-chloro-2-butyn-1-yl)cytosin, wherein B is cytosine-N$^1$-yl) was obtained as described above for the corresponding adenine derivative from 1.11 grams (10 mmol) of cytosine Compound 3 was obtained in 51% yield, 1 gram. Crystallization from 4:1 ethyl acetate-methanol afforded an analytical sample of melting point 198°–191° C.

UV (ethanol) max 272 nm (8,900), 206 (16,000).

$^1$H-NMR (CD3SOCD3), 7.61 (d, 1, H-6, cytosine), 7.17 (d, 2 NH2), 5.69 (d, 1, 4'5, cytosine), 4.54 and 4.45 (2d, H-1'and H-4').

Chemical ionization mass spectrum 198 (10.3, M), 162 (38.1, M-Cl).

Cytosine peaks L 111, 92, 81, and 69.

Calculated for C$_8$H$_8$ClN$_3$O: C, 48.62; H, 4.08; Cl, 17.94; N, 21.26.

Found: c, 48.71, H, 4.27; CL, 18.18; N, 21.26.

N$^1$-(4-hydroxy-2-butyn-1-yl)cytosine.

This compound was prepared according to the procedure for the corresponding adenine derivative starting from 5 mmol, 985 mg, of cytosine The crude product obtained after neutralization of the reaction mixture was Two methods were used to prepare N1-(4-hydroxy-1,2-butadien-1-yl) cytosine, also known as cytallene.

In method A, 716 mg or 4 mmol of compound 4 was refluxed in 0.1M sodium hydroxide in 30 ml of 20% aqueous dioxane for nine hours. The progress of isomerization was monitored by thin layer chromatography in 9:1 tetrahydrofuran-methanol, solvent S3. The layer was developed 3–4 times. After being cooled, the reaction mixture was worked up as described above for adenallene.

Chromatography in solvent S1 gave 200 mg (28% yield) of compound 1, wherein B=cytosin-N$^1$-yl as a single spot on thin layer chromatography with solvent S3, triple development. This material was crystallized from a minimum amount of methanol to give a product containing according to 1H-NMR from 10 to 14% of the starting material. Two more crystallizations afforded 94–97% pure compound, mp=186°–190° C.

UV max (pH 7) 290 nm (11,300), 224 (12,000), 204 (13,900). IR (KBr) 1965 cm$^{-1}$ (C=C=C).

$^1$H-NMR (CD$_3$SOCD$_3$) , 7.50 (d, 1, H-6, cytosine), 7.34 and 7.27 (overlapped signals, m, 3, NH$_2$ +H-1'), 6.12 (q. 1, H-3'), 5.80 (d, 1, H-5, cytosine), 5.05 (t, 1, OH), 4.03 (m, 2, H-4').

$^{13}$C-NMR 193.89 (C-2'), 99.31 (C-1'), 95.46 (C-3'), 59.08 (C-4').

Cytosine peaks: 165.43, 153.63, 140.85 and 106.83.

Chemical ionization mass spectrum: 180 (80.7, M+H), 162 (56.1, M−OH), 152 (14.3, M* —CH$_2$=CH, M* is a rearranged M from Scheme 3, =cytosin-n$^1$-yl), 125 (22.7), 97 (28.8).

Cytosine peaks: 111, 83, 69.

Calculated for C$_8$H$_9$N$_3$O$_2$: C, 53.62; H, 5.06; N, 23.45. Found: C, 53.42; H, 5.13; N, 23.33.

In Method B, the reaction was performed as for adenallene, Method B, with 268 mg or 1.5 mmol of the compound of formula 1, where B is cytosin-N$^1$-yl. The mixture was stirred under nitrogen from 14 hours at room temperature. The progress of the reaction was monitored by TLC in solvent S3 (triple development), and it was worked up in the usual fashion Chromatography afforded 214 mg, or 80% yield, of compound 1 where B is cytosin-$N^1$-yl, melting point 173°–180° C.

This product was crystallized to a constant melting point of 193°–195° C. (four times) from methanol as in Method A to give cytallene of >99% purity by $^1$H-NMR and identical by thin layer chromatography, melting point, and UV spectrum, with a sample prepared by Method A.

Example 3, Synthesis of $N^9$-(4-hydroxy-1,3-butadien-1-yl) hypoxanthine

A mixture of 100 mg, 0.5 mmol of adenallene (where B is adenin-$N^9$-yl) and 30 mg of adenosine deaminase from calf intestine (Type III, Sigma Chemical Co, St. Louis, MO) was magnetically stirred in 15 ml of 0.05M $Na_2HPO_4$ of pH 7.15 for fourteen hours.

The progress of deamination was followed by thin layer chromatography in solvent S1, double development. The solvent was evaporated and the solid residue was extracted by boiling with 25 ml of solvent S2 three times. The extract was evaporated and the crude product was chromatographed on a silica gel column in solvent S1 to give a compound formula 1, where B is hypoxanthin-$N^9$-yl, a 90% yield of 90 mg. This material was crystallized for analysis from 4:1 ethyl acetate-methanol, and had a melting point of 210° C. (decomposed).

UV (pH 7.0) max 222 nm (26,500).

$^1$H-NMR (CD$_3$SOCD$_3$), 12.40 (bs, 1, NH), 8.10 (2s, 2, H-2 and H-8, purine), 7.34 (m, 1, H-1'), 6.22 (q, 1, H-3'), 5.05 (bs, 1, OH), 4.12 (m, 2, H-4').

$^{13}$C-NMR 195.85 (C-2'), 106.14 (C-1'), 93.80 (C-3'), 58.73 (C-4').

Hypoxanthine peaks: 167.16, 156.43, 146.21, 137.90 and 124.36.

Calculated for $C_9H_8N_4O_2$: C, 52.93; H, 3.94; N, 27.44. Found: C, 52.62; H, 4.12; N, 27.27.

The compounds of formula 1 exhibit a significant antiretroviral activity. It was found that cytallene 1 and adenallene 1 strongly inhibit the infectivity and cytopathic effect of HIV at concentrations which do not interfere with the proliferation of the target cells. These effects are comparable with those of AZT (3'-azido-2',3'-dideoxythymidine, also known as zidovudine or retrovir), currently the only drug effective against AIDS which is currently available to patients, or with 2',3'-dideoxyadenosine and 2',3'-dideoxycytidine, nucleoside analogues which are currently undergoing clinical testing, as shown in FIGS. 1 and 2.

Figure 1B:
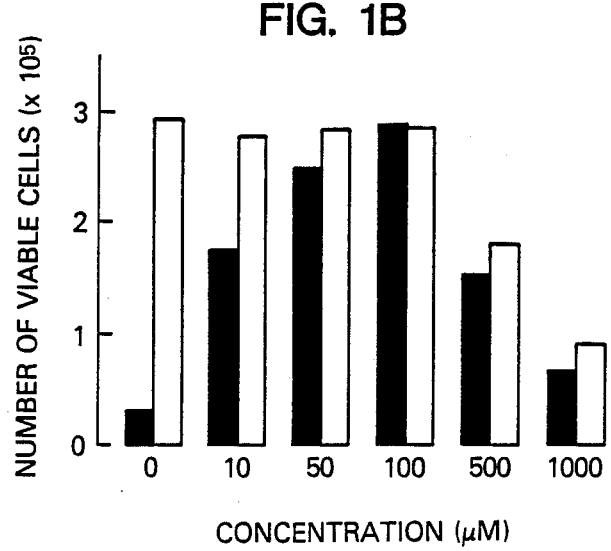

In FIG. 1, ATH8 cells ($2\times 10^5$) were exposed to HIV, 2000 virus particles per cell. The number of viable cells was determined, and was plotted against concentration of adenallene, panel B, solid columns. Control cells, open columns, were not exposed to the virus. A similar cytopathic effect of 2',3'-dideoxyadenosine is given for comparison in panel A.

In FIG. 2, the experiment with cytallene was performed in the same fashion as shown in FIG. 1 for adenallene, panel B. Again, data obtained with 2',3'-dideoxycytidine is given for comparison in panel A.

The latter figures indicate the extent of protection by cytallene or adenallese against the cytopathic effect of HIV on ATH8 cells. For comparison, results with 2',3'-dideoxyadenosine and 2',3'-dideoxycytidine are also given.

Figure 3:
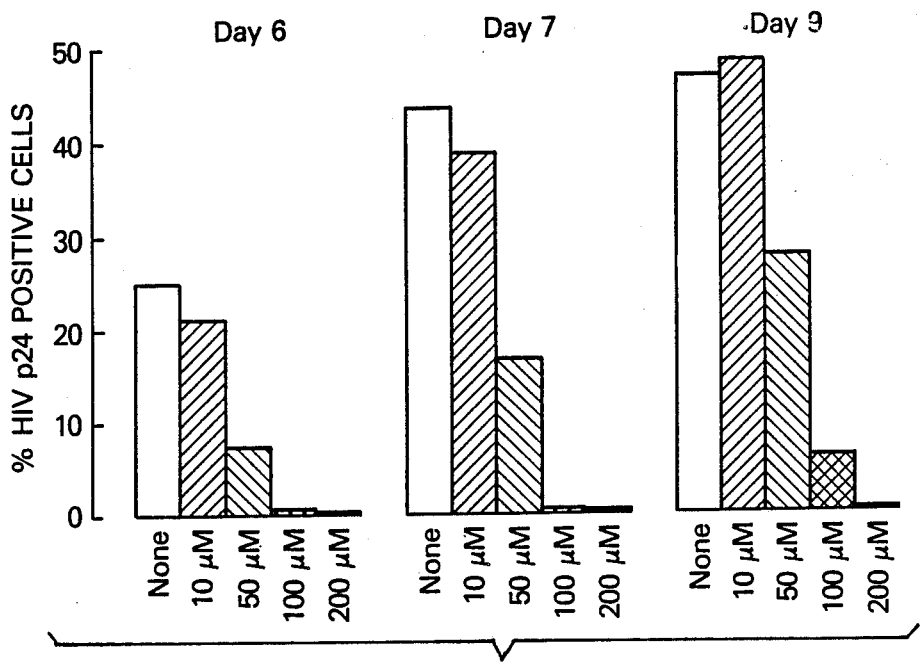
FIG. 3 shows the inhibition of infectivity and replication of HIV in H9 cells by adenallene.
Figure 4:
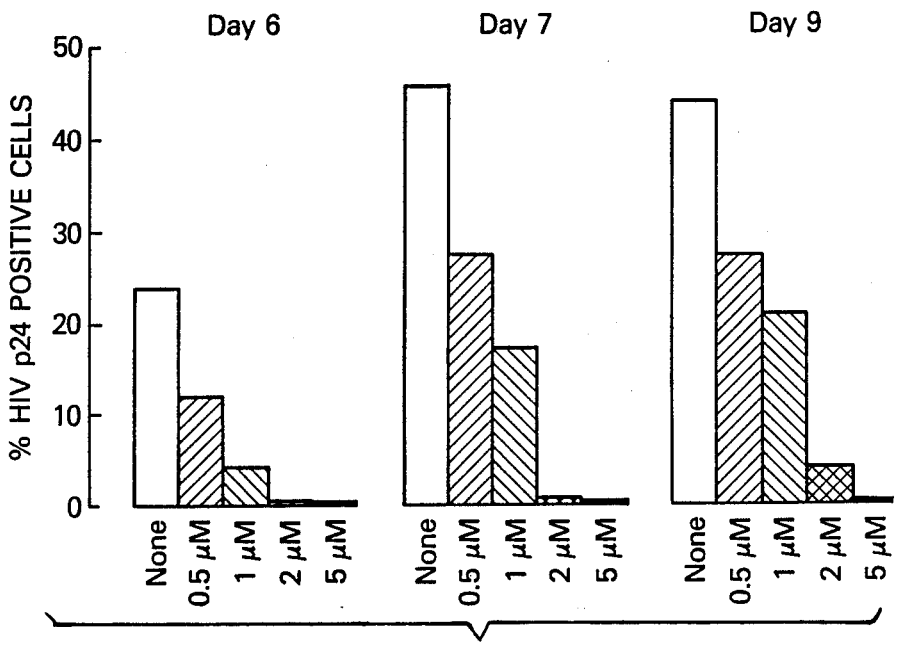
FIG. 4 shows the inhibition of infectivity and replication of HIV in H9 cells by cytallene.

The antiretroviral effect of cytallene and adenallene was confirmed by using the expression of HIV p24 gag protein in H9 cells, as shown in FIGS. 3 and 4, as a measure of inhibition of viral replication. It can be clearly seen that both analogues are potent inhibitors of replication of HIV virus in this system.

In FIG. 3, the H9 cells were exposed to HIV virus and then incubated with varying amounts of adenallene. On day 6, panel A, day 7, panel B, and day 9, panel C, the percentage of the target H9 cells expressing p24 gag protein of HIV was determined by indirect immunofluorescence assay.

In FIG. 4, the experiment with cytallene was performed as described in FIG. 3 for adenallene.

It should also be emphasized that both adenallene and cytallene are stable in solutions of strong acids. Thus, adenallene is unchanged at pH 1 (0.1M HCl) for sixteen hours at room temperature. This property is of particular importance in that the compounds can be administered orally The compounds of the present invention can be used therapeutically against AIDS viruses and their related disorders including the seropositive state, progressive generalized lymphadenopathy, AIDS-related complex, and AIDS-related neurologic disease.

Compositions within the scope of the invention include compositions wherein the component thereof is contained in an effective amount to achieve its intended purpose. Determination of the effective amounts is within the skill of the art. Preferred dosages, which are of course dependent upon the severity of the infection and the individual patient's response to the treatment, can range from about 0.01 to about 100 mg/kg of body weight to give a concentration in the blood ranging from about 0.05 microgram to about 5000 micrograms per ml. of whole blood By the term "pharmaceutically acceptable salts" is intended salts with pharmaceutically acceptable acids or bases, e.g., acids such as sulfuric, hydrochloric, acetic, phosphoric, etc., or bases such as alkali or alkaline earth metal hydroxide, ammonium hydroxides, alkylammonium hydroxides, etc.

In addition to the compounds of the present invention,, the pharmaceutical compositions may contain suitable pharmaceutically acceptable carriers comprising excipients and auxiliaries which facilitate processing of the active compounds into preparations which can be used pharmaceutically. Preferably, the preparations, particularly those which can be administered orally and which can be used for the preferred type of administration, such as tablets, dragees, and capsules, and also preparations which can be administered rectally, such as suppositories, as well as suitable solutions for administration by injection or orally contain from about 0.1 to 99 percent, preferably from about 25–85 percent of active compound, together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding a resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example, tricalcium phosphate or calcium hdyrogen phosphate, as well as binders such as starch paste, using, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone. If desired, disintegrating agents may be added such as the above-mentioned starches and also carboxymethylstarch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetyl-cellulose phthalate or hydroxypropylmethylcellulose phthalate, are used. Dyestuffs or pigments may be added to the tablets or dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved to suspended unsuitable liquids, such as fatty oils, liquid paraffin, or liquid polyethylene glycols. In addition, stabilizers may be used.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols or higher alkanols. In addition, it is also possible to use gelatin rectal capsules which consist of a combination of the active compounds with a base. Possible base material include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspension of the active compounds as appropriate oily injection suspensions may be administered. Suitable lipophilic solvents or vehicles include fatty oils, such as sesame oil, or synthetic fatty acid esters, for example, ethyl oleate or triglycerides. Aqueous injection suspensions may contain substances which increase the viscosity of the suspension such as sodium carboxymethylcellulose, sorbitol, and/or dextran. Optionally, the suspension may also contain stabilizers.

Alternatively, the active ingredients of the present invention may be administered in the form of liposomes, pharmaceutical compositions wherein the active ingredient is contained either dispersed or variously present in corpuscles consisting of aqueous concentrate layers adherent to hydrophobic lipidic layer. The active ingredient may be present both in the aqueous layer and in the lipidic layer, or, in the non-homogeneous system generally known as a liposomic suspension.

Of course, the present invention is not limited to the specific embodiments herein described, but includes any variation or modification that is within the scope of one skilled in the art.

What is claimed is:

1. A compound selected from the group consisting of $N^9$-(4-hydroxy-1,2-butadien-1-yl)adenine and $N^1$-(4-hydroxy-1,2-butadien-1-yl)cytosine and pharmaceutically acceptable salts thereof.

2. A pharmaceutical composition comprising a compound of claim 1 and a pharmaceutically acceptable carrier.

3. A method of treating mammals inflected with a retrovirus comprising administering an anti-retrovirally effective amount of a compound of claim 1.

4. The method of claim 3 wherein said mammal is a human and said retrovirus is the human immunodeficiency virus.

* * * * *